US009119780B2

(12) United States Patent
Song et al.

(10) Patent No.: US 9,119,780 B2
(45) Date of Patent: Sep. 1, 2015

(54) TRIGGERABLE COMPOSITIONS FOR TWO-STAGE, CONTROLLED RELEASE OF PROACTIVE CHEMISTRY

(71) Applicant: Kimberly-Clark Worldwide, Inc., Neenah, WI (US)

(72) Inventors: Xuedong Song, Alpharetta, GA (US); Yiming Weng, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/066,856

(22) Filed: Oct. 30, 2013

(65) Prior Publication Data

US 2015/0118294 A1     Apr. 30, 2015

(51) Int. Cl.
*A61K 31/455* (2006.01)
*A61K 31/07* (2006.01)
*A61K 31/05* (2006.01)
*A61K 8/11* (2006.01)
*A61K 8/49* (2006.01)
*A61K 8/81* (2006.01)
*A61Q 19/00* (2006.01)
*C11B 9/00* (2006.01)
*A61K 47/48* (2006.01)

(52) U.S. Cl.
CPC .............. *A61K 8/11* (2013.01); *A61K 8/4926* (2013.01); *A61K 8/8152* (2013.01); *A61K 8/8182* (2013.01); *A61K 31/05* (2013.01); *A61K 31/07* (2013.01); *A61K 31/455* (2013.01); *A61K 47/48107* (2013.01); *A61Q 19/00* (2013.01); *C11B 9/0015* (2013.01); *A61K 2800/548* (2013.01); *A61K 2800/56* (2013.01)

(58) Field of Classification Search
CPC ..... A61K 31/455; A61K 31/07; A61K 31/05; A61K 47/48107; A61K 9/0002
See application file for complete search history.

(56) References Cited

U.S. PATENT DOCUMENTS

| 4,020,156 | A | 4/1977 | Murray et al. |
|---|---|---|---|
| 4,540,564 | A | 9/1985 | Bodor |
| 4,880,921 | A | 11/1989 | Bodor |
| 5,130,290 | A | 7/1992 | Tanimoto |
| 5,133,958 | A | 7/1992 | Stuckler |
| 5,197,958 | A | 3/1993 | Howell |
| 5,389,093 | A | 2/1995 | Howell |
| 5,622,944 | A | 4/1997 | Hale et al. |
| 5,827,913 | A | 10/1998 | Baetzold et al. |
| 5,958,870 | A | 9/1999 | Declercq et al. |
| 6,369,290 | B1 | 4/2002 | Glaug et al. |
| 6,458,456 | B1 | 10/2002 | Zainiev et al. |
| 6,586,639 | B2 | 7/2003 | Murayama et al. |
| 6,677,297 | B2 | 1/2004 | Frerot |
| 7,056,878 | B2 | 6/2006 | Fender et al. |
| 7,105,715 | B2 | 9/2006 | Carlucci et al. |
| 7,229,958 | B2 | 6/2007 | Kohle et al. |
| 7,407,670 | B2 | 8/2008 | Six et al. |
| 7,501,536 | B2 | 3/2009 | Jaunky et al. |
| 7,550,416 | B2 | 6/2009 | Woo et al. |
| 7,655,830 | B2 | 2/2010 | Flohr et al. |
| 7,758,888 | B2 | 7/2010 | Lapidot et al. |
| 8,022,030 | B2 | 9/2011 | Berthier et al. |
| 2003/0083513 | A1 | 5/2003 | Murayama et al. |
| 2004/0110891 | A1 | 6/2004 | Guo et al. |
| 2004/0234597 | A1 | 11/2004 | Shefer et al. |
| 2005/0131363 | A1 | 6/2005 | Kim et al. |
| 2007/0021319 | A1 | 1/2007 | Kohle et al. |
| 2007/0031485 | A1 | 2/2007 | Ljusberg-Wahren et al. |
| 2007/0081953 | A1 | 4/2007 | Dahms |
| 2007/0105793 | A1 | 5/2007 | Hendrix |
| 2007/0160553 | A1 | 7/2007 | Kripp et al. |
| 2007/0270773 | A1 | 11/2007 | Mackey |
| 2008/0139378 | A1 | 6/2008 | Hildebrand et al. |
| 2008/0221173 | A1 | 9/2008 | Bhaskaran et al. |
| 2008/0279253 | A1 | 11/2008 | MacDonald et al. |
| 2008/0286224 | A1 | 11/2008 | Vega et al. |
| 2009/0054860 | A1 | 2/2009 | Young et al. |

(Continued)

FOREIGN PATENT DOCUMENTS

| EP | 0 752 465 A1 | 1/1997 |
|---|---|---|
| EP | 0 771 785 B1 | 1/2002 |

(Continued)

OTHER PUBLICATIONS

Co-pending U.S. Appl. No. 13/230,102, filed Sep. 12, 2011, by Song et al. for "Wetness Indicator Having Varied Hues."
Co-pending U.S. Appl. No. 13/292,612, filed Nov. 9, 2011, by Wei et al. for "Non-Tacky Wetness Indicator Composition for Application on a Polymeric Substrate."
Co-pending U.S. Appl. No. 13/671,291, filed Nov. 7, 2012, by Song for "Triggerable Compositions for Two-Stage, Controlled Release of Active Chemistry."
Lindstedt, M. et al., "Antimicrobial Activity of Betaine Esters, Quaternary Ammonium Amphiphiles Which Spontaneously Hydrolyze into Nontoxic Components," Antimicrobial Agents and Chemotherapy, vol. 34, No. 10, Oct. 1990, pp. 1949-1954.

*Primary Examiner* — Abigail Fisher
(74) *Attorney, Agent, or Firm* — Kimberly-Clark Worldwide, Inc.

(57) ABSTRACT

A triggerable composition for two-stage, controlled release of a functional active chemical includes a trigonelline ester of a functional active with at least one hydroxyl group configured to release the functional active through a hydrolysis reaction upon contact with an aqueous medium, and an encapsulation material for encapsulating the trigonelline ester including a functional active, the encapsulation material triggerable to release the trigonelline ester upon the occurrence of an environmental stimulus. In other aspects, a viscous liquid or an absorbent article includes a triggerable composition for two-stage, controlled release of a functional active chemical, the composition including a trigonelline ester of a functional active with at least one hydroxyl group configured to release the functional active through a hydrolysis reaction upon contact with an aqueous medium, and an encapsulation material for encapsulating the trigonelline ester including a functional active.

13 Claims, No Drawings

(56) References Cited

U.S. PATENT DOCUMENTS

| | | |
|---|---|---|
| 2009/0156634 A1 | 6/2009 | Molino et al. |
| 2009/0221980 A1 | 9/2009 | Mosbacher et al. |
| 2009/0275906 A1 | 11/2009 | Berland et al. |
| 2009/0275908 A1 | 11/2009 | Song |
| 2010/0012017 A1 | 1/2010 | Miller |
| 2010/0030173 A1 | 2/2010 | Song et al. |
| 2010/0160299 A1 | 6/2010 | Baker, Jr. et al. |
| 2010/0221330 A1 | 9/2010 | Messadek |
| 2010/0227896 A1 | 9/2010 | Biedermann et al. |
| 2010/0248959 A1 | 9/2010 | Kato et al. |
| 2010/0307422 A1 | 12/2010 | Huck et al. |
| 2011/0015599 A1 | 1/2011 | Song et al. |
| 2011/0046571 A1 | 2/2011 | Waldhorn |
| 2011/0104023 A1 | 5/2011 | Nakatsubo et al. |
| 2011/0144603 A1 | 6/2011 | Song |
| 2011/0152805 A1 | 6/2011 | Gil |
| 2011/0250286 A1 | 10/2011 | Marcello et al. |
| 2012/0064136 A1 | 3/2012 | Baker, Jr. et al. |
| 2012/0121669 A1 | 5/2012 | Fontana et al. |
| 2012/0259098 A1 | 10/2012 | Baker, Jr. et al. |
| 2013/0018076 A1 | 1/2013 | Friedel et al. |

FOREIGN PATENT DOCUMENTS

| | | |
|---|---|---|
| JP | 01-275511 A | 11/1989 |
| JP | 03-221039 A | 9/1991 |
| WO | WO 98/26808 A2 | 6/1998 |
| WO | WO 01/27234 A1 | 4/2001 |
| WO | WO 03/047558 A2 | 6/2003 |
| WO | WO 2008/068059 A2 | 6/2008 |
| WO | WO 2009/018368 A1 | 2/2009 |
| WO | WO 2010/088053 A2 | 8/2010 |
| WO | WO 2012/094636 A2 | 7/2012 |
| WO | WO 2013/016257 A1 | 1/2013 |

TRIGGERABLE COMPOSITIONS FOR TWO-STAGE, CONTROLLED RELEASE OF PROACTIVE CHEMISTRY

BACKGROUND

The present disclosure pertains to a composition that controls the chemical release of functionally active components from a previously inactive and modified state. In particular, the present disclosure pertains to a composition that gradually or rapidly releases active chemical components upon the occurrence of specific environmental stimuli. The composition can be used in bandages, hygiene products, health care products and skin-contacting beauty products, as well as in consumer product applications. The present disclosure also relates to such bandages, hygiene products, health care products, beauty products and consumer products incorporating such chemistry.

A large number of functionally active chemicals are known for use with personal care and beauty products, hygiene products, health care related products, and skin-contacting products. For example, such actives include antimicrobial or antibacterial agents, antioxidant agents, antiseptic-type agents, skin-repairing agents, and fragrances. Unfortunately, many of these functionally-active chemicals are not stable or do not have ideal properties under various environmental conditions. For example, if such actives include volatile components such as those found in fragrances, they can dissipate into the surrounding environment upon exposure to air and humidity conditions. Therefore, such chemicals can demonstrate short shelf lives when in use, and can present serious packaging/storage concerns. As a result, costly packaging can be necessary for products incorporating such chemicals. This instability creates a significant limitation on the wide adoption of the potentially useful chemistry and limits the long-term efficacy of products incorporating such chemistry. Further, processing challenges such as elevated temperatures can exist, and, as a result, can present a need to limit exposure to environmental stimuli during manufacture.

Additional challenges presented by the use of such active chemicals include the difficulties involved with gradually controlling the release of such active chemicals, as well as the potential side effects and costs resulting from use of chemically degraded products. Other actives, such as antioxidants, are also often not stable when exposed to ambient conditions, such as the air of a user's pantry or storage closets. Antioxidants can readily be oxidized by oxygen in the air. Some skin-repairing chemicals are also not stable when exposed to the surrounding environment. For example, the skin-repairing agent retinol is not stable under ambient conditions without protection from the environment. In fact, it can become a skin irritant when its concentration is relatively high. Currently no proactive technology has emerged to be very effective to achieve both property modification and at the same time release-on-demand under mild conditions. For example, anti-oxidants such as vitamin C and vitamin A are often stabilized through the ester forms which are hydrolyzed into the active forms through enzymes when digested into bodies. In many cases, a large portion of the actives are wasted because they are not hydrolyzed and released to the desired locations. A need therefore exists for a versatile composition that effectively stabilizes functional chemical actives, and releases such actives upon demand, at a desirable rate and profile.

Attempts have been made to overcome the stability and storage limitations presented by such actives. For example, some have suggested stabilizing retinol by encapsulating it in pH-sensitive polymers and then releasing it at a later time by changing the solubility of the encapsulating matrix through a pH change. The encapsulated retinol still suffers significant degradation, presumably from oxidation. Others have suggested converting retinol into an ester as a proactive (a precursor to the retinol active), and then at a later time converting the ester into the active form by use of enzymes present in a user's body after delivery through a user's skin. With such methodology, however, only a small portion of the ester is used effectively by the skin layer and a majority of the esters are wasted by the system. Such a system can also actually lead to side effects when too much retinol ester is used to achieve effective dosages on the skin. Therefore, a need still exists for delivery compositions for skin-repair actives.

In connection with the delivery of fragrances (such as in connection with personal care absorbent products), it has been suggested to encapsulate fragrances in polymeric matrices for stabilization and delivery benefits. Even with such encapsulation technology, however, there is a further need for fragrance encapsulation technology that offers effective protection for such volatiles as well as a controlled release. Existing encapsulation chemistries for consumer products often leak or release prematurely. A continuing need exists for a material composition that both provides stability for unstable actives, and that provides for release of actives in a controlled manner.

SUMMARY

The current disclosure is directed to a triggerable composition for creating a stable, controlled-release of functional chemical active components using a two-stage release mechanism. The graduated or rapid release of functional chemical active components allows for protection of the functional actives from the surrounding environment, as well as the selective release of such actives upon the occurrence of two select environmental stimuli. The protection and stabilization of the functional active is accomplished through esterification of the functional active into a trigonelline ester molecule, as well as the incorporation of the modified trigonelline ester molecule into an encapsulation polymer matrix. Subsequent triggered release of the functional active from the trigonelline ester molecule is dependent upon preselected properties of the encapsulation polymer matrix (first stage trigger), as well as the hydrolysis of the trigonelline ester (by an aqueous medium, in a second stage trigger) once the trigonelline ester molecule is released or freed from the encapsulation polymer matrix. For the purposes of this application, the term "aqueous medium" means a medium containing "liquid" water as opposed to water vapor. Such aqueous medium is exemplified by but not limited to urine, sweat, vaginal fluids, mucous, menses, and runny, liquid, and loose bowel movements.

The functional active chemicals can be a fragrance, a skin-repairing agent, an antioxidant agent, an antimicrobial/antibacterial agent, an antifungal agent, a hormone, and a medically active agent. Stabilization of the functional active chemicals through a trigonelline ester molecule and within an encapsulation polymer matrix prevents the premature release of the chemicals either into the environment or to a desired location. The functional active chemicals can be derived from substances including at least one hydroxyl group that are volatile, water-sensitive, or easily oxidized by oxygen. The stabilization is specifically accomplished by the incorporation of a radical form of the functional active chemicals into the trigonelline ester. The ester bond connecting the radical (R) of the functional active to the trigonelline portion of the molecule in the trigonelline ester can be readily hydrolyzed upon exposure to an aqueous medium to release the active. The encapsulation polymer matrix protecting the trigonelline ester can be designed to be sensitive to water in either a neutral, acidic, or basic condition. The encapsulation polymer matrix protecting the trigonelline ester can also be designed to be sensitive to enzymes, ions, or ligands.

In one aspect of the disclosure, a triggerable composition for two-stage, controlled release of a functional active chemical includes a trigonelline ester of a functional active with at least one hydroxyl group configured to release the functional active through a hydrolysis reaction upon contact with an aqueous medium, and an encapsulation material for encapsulating the trigonelline ester including a functional active, the encapsulation material triggerable to release the trigonelline ester upon the occurrence of an environmental stimulus.

In an alternative aspect of the disclosure, an absorbent article includes at least one absorbent layer and a triggerable composition for two-stage, controlled release of a functional active chemical, the triggerable composition including a trigonelline ester of a functional active with at least one hydroxyl group configured to release the functional active through a hydrolysis reaction upon contact with an aqueous medium; and an encapsulation material for encapsulating the trigonelline ester including a functional active, the encapsulation material triggerable to release the trigonelline ester upon the occurrence of an environmental stimulus.

In yet another alternative aspect of the disclosure, a viscous liquid includes a triggerable composition for two-stage, controlled release of a functional active chemical, the composition including a trigonelline ester of a functional active with at least one hydroxyl group configured to release the functional active through a hydrolysis reaction upon contact with an aqueous medium, and an encapsulation material for encapsulating the trigonelline ester including a functional active, the encapsulation material triggerable to release the trigonelline ester upon the occurrence of an environmental stimulus, wherein the viscous liquid is a lotion, cream, or medicament.

In another aspect of the disclosure, a triggerable composition for two-stage, controlled release of a functional active chemicals includes a trigonelline ester for release of a functional active contained on the trigonelline ester, through a hydrolysis reaction upon contact with an aqueous medium, and an encapsulation material for encapsulating the trigonelline ester including a functional active, the encapsulation material triggerable to release the trigonelline ester upon the occurrence of an environmental stimulus, wherein the environmental stimulus is a pH change.

Other features and aspects of the present disclosure are discussed in greater detail below.

DETAILED DESCRIPTION

In general, the present disclosure is directed to a composition that includes an encapsulation chemistry for selectively releasing a functional active through a trigonelline ester and stimuli-sensitive encapsulation chemistries. The selective triggering of the encapsulation chemistries will expose the trigonelline ester to an aqueous medium. In a second stage, upon exposure of the trigonelline ester to the aqueous medium, a hydrolysis reaction will occur, resulting in the release of the functional active from the trigonelline ester into the surrounding environment or at a targeted location. The surrounding environment or targeted location can be onto a user's skin, or into the structure of an article containing the triggerable composition. Such article can be, for example, a health care product such as a garment or bandage, a hygiene product such as a tissue or wipe, a skin-contacting beauty product such as a facial wrap, an absorbent consumer/personal care article such as a feminine care pad or liner, a baby or child care diaper, or an adult incontinence garment. The composition of the disclosure can further be present in a viscous liquid such as a lotion, cream, or medicament as well.

The functional active chemistry of the composition can be a fragrance, an antioxidant, an antimicrobial or antibacterial agent, or a skin-repairing agent. The functional active has a hydroxyl group in its molecular structure. The functional active chemicals are converted into a trigonelline ester. The rationale for converting the active (R*OH chemical) into an ester form of trigonelline is to modify the properties of the active. There are several properties of actives that can be modified by this structural change, such as volatility (and consequential difficulty in storage, handling and processing). The ester form of the active would be nonvolatile. The property of oxidation can also be controlled by conversion of a material into the trigonelline ester form. Antioxidants and skin-repair agents (such as retinol) can also be placed in a more stable form when converted into a trigonelline ester. Further, some actives demonstrate poor solubility (such as thymol) that has low bioavailability. The trigonelline ester forms can improve water solubility of these actives. Some actives demonstrate poor permeability (such as retinol) through biological barriers such as skin cells. The trigonelline ester form of such actives can be used to balance the hydrophilicity/hydrophobicity of the active to improve skin permeability. The trigonelline ester form can also be used to control the release rate of an active.

For the purposes of this description, a suitable trigonelline ester shall be described by the general formula of:

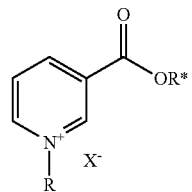

R = CH$_3$, C$_3$H$_7$, C$_5$H$_{11}$, C$_7$H$_{15}$

R is an organic moieties such as alkyl or its derivatives with functional groups. R*OH is an active. X— is an counter ion. The ester bond can be hydrolyzed under mild conditions to generate ROH upon exposure to moisture or aqueous media or hydrolases. The trigonelline ester is an ester of trigonelline and the functional active chemistry with one or more hydroxyl groups. That is, the (R*) group is a radical of the functional active, such as the radical of a volatile fragrance alcohol with one or more hydroxyl groups. The (R*) group includes components having the desired functionality. For example, if such (R*) group is a fragrance alcohol group component, it includes components having odiferous properties.

The R group can be an alkyl group with a formula of (CH$_2$)$_n$CH$_3$. It should also be recognized that the larger the value for "n," the more difficult also for the trigonelline ester to solubilize in water as well as undergo hydrolysis. Further, the more hydrophilic the R group, the less stable the trigonelline ester with associated (R*) group is, in the sense that it is more likely that vapor/humidity in the air alone will cause the disassociation of the (R*) group (such as fragrance alcohol) from the trigonelline ester molecule. Further, if the trigonelline ester is too hydrophobic; that is, if it includes large hydrophobic groups in the R group, the more likely that it will not be water soluble, or less so. The (R*) group can include radicals of nonfragrance functional components, such as retinol, which is attached at the ester linkage.

As noted, it is desirable that the trigonelline ester is not large (not including an "n" number larger than 4, that it is not part of a larger polymer structure, and not itself bonded as a functional group, to a chain base structure) such that it can be easily solubilized, and not be so hydrophobic in nature that it would be difficult to process, and would impact aqueous liquid flow on a coated absorbent substrate. Further, if the trigonelline ester is too large, in that it includes larger groups in its R positions, or is part of a larger structure, it has been found that the hydrolysis reaction time is slower. In a desirable aspect, such trigonelline ester includes only hydrogen or alkyl carbon-based moieties in its R groups.

In one aspect, the functional active (radical of the fragrance alcohol aspect) of the (R*) group is selected from the fragrance group including 4-allyl-2-methoxyphenol (eugenol), 3-(2-bornyloxy)-2-methyl-1-propanol, 2-tert-butylcyclohexanol, 4-tert-butylcyclohexanol, benzyl alcohol, 1-decanol, 9-decen-1-ol, dihydroterpineol, 2,4-dimethyl-4-cyclohexen-1-yl methanol, 2,4-dimethylcyclohexyl methanol, 2,6-dimethyl-2-heptanol, 2,6-dimethyl-4-heptanol, 3a,4,5,6,7,7a-hexahydro-2,4-dimethyl-4,7-methano[1H]inden-5-ol, 3,7-dimethyl-1,6-nonadien-3-ol, 2,6-dimethyl-2,7-octadien-6-ol (linalool), cis-3,7-dimethyl-2,6-octadien-1-ol (nerol), trans-3,7-dimethyl-2,6-octadien-1-ol (geraniol), 3,7-dimethyl-1,7-octanediol, 3,7-dimethyl-1-octanol (tetrahydrogeraniol), 2,6-dimethyl-2-octanol (tetrahydromyrcenol), 3,7-dimethyl-3-octanol (tetrahydrolinalool), 2,6-dimethyl-7-octen-2-ol (dihydromyrcenol), 3,7-dimethyl-6-octen-1-ol (citronellol), 2,2-dimethyl-3-(3-methylphenyl)-1-propanol, 2,2-dimethyl-3-phenyl-1-propanol, 2-ethoxy-4-methoxymethylphenol, 2-ethyl-4-(2,2,3-trimethyl-3-cyclopenten-1-yl)-2-buten-1-ol, cis-3-hexen-1-ol, 4-(4-hydroxy-3-methoxyphenyl)-2-butanone, 1-hydroxy-2-(1-methyl-1-hydroxyethyl)-5-methyl-cyclohexane, 3-(hydroxymethyl)-2-nonanone, 4-(4-hydroxy-4-methylpentyl)-3-cyclohexene-1-carboxaldehyde, isoborneol, 3-isocamphylcyclohexanol, 2-isopropenyl-5-methylcyclohexanol (isopulegol), 1-isopropyl-4-methylcyclohex-3-enol (terpinenol), 4-isopropylcyclohexanol, 1-(4-isopropylcyclohexyl) ethanol, 4-isopropylcyclohexylmethanol, 2-isopropyl-5-methylcyclohexanol (menthol), 2-isopropyl-5-methylphenol (thymol), 5-isopropyl-2-methylphenol (carvacrol), 2-(4-methyl-3-cyclohexenyl)-2-propanol (terpineol), 2-(4-methylcyclohexyl)-2-propanol (dihydroterpineol), 4-methoxybenzyl alcohol, 2-methoxy-4-methylphenol, 3-methoxy-5-methylphenol, 1-methoxy-4-propenylbenzene (anethol), 2-methoxy-4-propenylphenol (isoeugenol), 4-methyl-3-decen-5-ol, 2-methyl-6-methylene-7-octen-2-ol (myrcenol), 3-methyl-4-phenyl-2-butanol, 2-(2-methylphenyl) ethanol, 2-methyl-4-phenyl-1-pentanol, 3-methyl-5-phenyl-1-pentanol, 2-methyl-1-phenyl-2-propanol, (1-methyl-2-(1,2,2-trimethylbicyclo[3.1.0]hex-3-ylmethyl) cyclopropyl) methanol, 3-methyl-4-(2,2,6-trimethylcyclohexen-1-yl)-2-butanol, 2-methyl-4-(2,2,3-trimethyl-3-cyclopenten-1-yl)-2-buten-1-ol, (3-methyl-1-(2,2,3-trimethyl-3-cyclopentenyl)-3-cyclohexen-1-yl) methanol, 3-methyl-5-(2,2,3-trimethyl-3-cyclopenten-1-yl)-4-penten-2-ol, 2-methyl-2-vinyl-5-(1-hydroxy-1-methylethyl) tetrahydrofuran, trans, cis-2,6-nonadienol, 1-nonanol, nopol, 1,2,3,4,4a,5,6,7-octahydro-2,5,5-trimethyl-2-naphthol, 1-octanol, 3,4,5,6,6-pentamethyl-2-heptanol, 2-phenylethanol, 2-phenylpropanol, 3-phenylpropanol (hydrocinnamic alcohol), 3-phenyl-2-propen-1-ol (cinnamic alcohol), 4-(5,5,6-trimethylbicyclo[2.2.1]hept-2-yl)cyclohexan-1-ol, 3,5,5-trimethylcyclohexanol, 2,4,6-trimethyl-4-cyclohexen-1-ylmethanol, 5-(2,2,3-trimethyl-3-cyclopentenyl)-3-methylpentan-2-ol, 3,7,11-trimethyl-2,6,10-dodecatrien-1-ol (farnesol), 3,7,11-trimethyl-1,6,10-dodecatrien-3-ol (nerolidol), 3,5,5-trimethyl-1-hexanol (isononanol), 1-undecanol, 10-undecen-1-ol, and vetiverol.

In another desirable aspect, the fragrance active group (R*) on the trigonelline ester is derived from 2-phenoxyethanol, phenylethylalcohol, geraniol, citronellol, 3-methyl-5-phenyl-1-pentanol, 2,4-dimethyl-3-cyclohexene-1-methanol, linalool, tetrahydrolinalool, 1,2-dihydromyrcenol, hydroxycitronellal, farnesol, menthol, eugenol, thymol, vanillin, cis-3-hexenol, terpineol, or mixtures thereof.

An example of a particularly desirable fragrance active (R*) group that is attached to the trigonelline ester is the radical of eugenol. Eugenol itself is represented by the following formula:

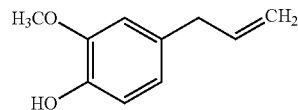

Other particularly desirable (R*) groups from volatile fragrance alcohols include radicals of menthol and thymol, with thymol offering the additional advantage of providing potential antibacterial functionality to the absorbent article or other article on which it is coated, or the lotion, cream, or medicament composition in which it is present.

While such fragrance volatiles are actively volatile in their disassociated alcohol state, such volatility is eliminated once their radicals are attached as part of the trigonelline ester at the (R*) location. The relative hydrophobicity and hydrophilicity of the R groups can be easily adjusted to tailor the hydrolysis rate upon exposure to aqueous medium, and therefore the release rate of the active R*OH. The trigonelline esters (where desirably R is a methyl group and X— is Cl) of menthol and thymol have been found to be hydrolyzed rapidly upon exposure to liquid water under ambient conditions. However, the trigonelline ester derivatives (where R is $C_8H_{17}$) of menthol and thymol have been found to be hydrolyzed at a much slower rate under the same conditions.

The "X" anions have no caustic or markedly irritating effect on human or animal skin, and are desirable for use in the composition, coating, or lotion/cream/medicament formulation for association with the trigonelline ester. The anions are desirably chosen from the group including chloride, bromide, methyl sulfate, ethyl sulfate, sulfate, nitrate, phosphate, and hydrogen phosphate.

As noted, once the trigonelline ester with attached functional active (such as fragrance radical moiety) has been synthesized, it has been found that the trigonelline ester is not volatile and is stable in the absence of an aqueous medium. This is especially the case for trigonelline esters in which the R group includes at least 8 carbons in total, in their structures. Following the introduction of the trigonelline ester to an aqueous medium, it undergoes a hydrolysis reaction in which the fragrance separates from the trigonelline ester and is released as an active fragrance volatile.

The resulting byproducts are either trigonelline or its derivatives and an active alcohol or volatile fragrance alcohol ((R—OH) structure), with the latter released into the article or surrounding environment to produce an effect or smell. Trigonelline and its derivatives are considered to be non-hazardous.

In general, trigonelline esters, their derivatives, and their preparation are known, and as such, the synthesis steps of particular trigonelline esters with radical groups (such as fragrance radicals) will not be further delineated. Examples of relatively smaller trigonelline ester molecules with attached fragrance radicals (radical groups of volatile alcohols) can also be found. It has now been found, however, that such chemistry is particularly well suited as a base chemistry for an active delivery formulation on various substrates and absorbent articles and in various formulations, particularly if such trigonelline esters are limited in size and do not severely impact absorbency pathways either as a result of their level of hydrophobicity or particular placement on a substrate or within an absorbent article.

Desirably, in one aspect, the trigonelline ester with attached chemical active is present in the composition (such as a coating) in an amount between about 0.1 and 30% by weight, alternatively, between about 0.5 to about 15 weight %, further alternatively, between about 1 to 10 weight %. The weight percentages given for this and further composition components are based on the total weight of the dried composition. It should be recognized that some compositions of the disclosure will initially utilize organic solvents for initial application of the composition to substrates, although such solvents are contemplated as being dried off during manufacture. Further, it is contemplated that such compositions can also be applied to substrates as hot melted coatings.

As a result of the moisture/aqueous media sensitivity of certain trigonelline esters as noted above, for those trigonelline esters with hydrogen or lower alkyl R groups, it can be desirable to insulate the trigonelline ester from moisture and aqueous medium before use, so as to delay release of functional active chemicals from hydrolysis. This delay of functional active release can be accomplished by encapsulating the trigonelline ester in an encapsulating polymer matrix. The encapsulating matrix can be either dissolved/degraded by aqueous media or alternatively, or can be swollen by water to expose the trigonelline esters to water for hydrolysis under various conditions.

The encapsulation chemistry of the present composition desirably is triggerable by the occurrence of one or more stimuli to free up the trigonelline ester protected by the encapsulation chemistry. Such encapsulation chemistry (encapsulation polymer matrix) can be in the form of a continuous cover of polymer/particles, microparticles, nanoparticles, encapsulation polymer coating sheets, films, fibers, laminates, foams, pastes, tablets, or suppositories. In such an instance, encapsulating polymers can act as the encapsulation matrix in which the trigonelline esters or trigonelline ester derivatives are embedded throughout the whole polymer matrix. Alternatively, such encapsulation chemistry can be a shell of a core/shell configuration, such that an encapsulating polymer shell surrounds the trigonelline ester core. Such encapsulation chemistry desirably is triggered by pH changes in the environment, but can also be triggered by enzymatic changes, solubility change, changes in temperature via thermogels, changes in ionic concentration, and changes in ligand chemistry.

There are a number of polymers that can used to achieve this protection through encapsulation of the trigonelline esters and derivatives of trigonelline esters. For example, in one aspect, dextrans and derivatives can be blended with trigonelline esters or trigonelline ester derivatives to form films. Upon contact with an aqueous medium, the dextran and derivatives can be dissolved and the trigonelline ester then exposed to water for hydrolysis, thereby releasing the functional active.

Environmentally triggerable encapsulation materials that are triggerable upon specific environmental stimuli can include copolymers of methacrylic acid and methyl methacrylate, which are sensitive to basic aqueous solutions. Such materials are available under the trade designations EUDRAGIT S-100 and L-100, available from Degussa. Alternatively, a copolymer based on dimethylaminoethyl methacrylate, butyl methacrylate, and methyl methacrylate that is sensitive to acidic aqueous solutions can be used. Such materials are available under the trade designation EUDRAGIT E-100 for example, from Degussa. Further encapsulation materials can include vinylpyrrolidone/vinyl acetate copolymers that are sensitive to neutral aqueous solutions. For example, such are available under the trade designations PVP/VA 1-335 from Ashland/ISP.

Certain polymers that are sensitive to basic aqueous solutions, such as copolymers of methacrylic acid and methyl methacrylate, are particularly effective encapsulation chemistry for use with trigonelline esters of thymol, menthol, and eugenol to minimize water sensitivity and solubility under certain pH. For example, when such trigonelline ester and polymer films are exposed to neutral water, little menthol, thymol, or eugenol is released. Upon exposure to alkaline aqueous solutions (such as of pH 9), however, such actives are steadily released. Similar performance can be demonstrated for films made from such trigonelline esters and a copolymer based on dimethylaminoethyl methacrylate, butyl methacrylate, and methyl methacrylate when exposing such films to first neutral aqueous solutions, and then to slightly acidic solutions (pH 5.5).

By using a composition having encapsulation material that is triggered by a specific change in the environment, such as for example, contact with vaginal fluids that might be excreted from a user with a vaginal infection, or for contact with other basic or slightly basic environments, the first stage trigger can be activated, thereby freeing up potential access to the second stage trigger of the trigonelline ester. For example, particular ailments can raise the pH level of vaginal secretions from a normally acidic level to a neutral or slightly alkaline level. Under normal conditions in which pH of such secretions is acidic, such encapulation chemistry would not be triggered. However, once vaginal fluid of a neutral or slightly alkaline level is introduced to the encapsulation chemistry triggered by a neutral or slightly alkaline environment, the encapsulation chemistry would allow for the release of trigonelline esters or trigonelline ester derivatives. Upon continued contact of the trigonelline esters or trigonelline ester derivatives with an aqueous medium, the functional active on the trigonelline ester would be released.

Examples of various encapsulation chemistries useful in the disclosure are illustrated below.

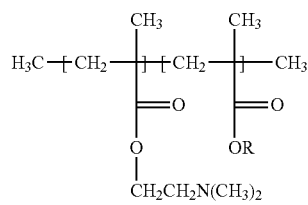

EUDRAGIT E-100

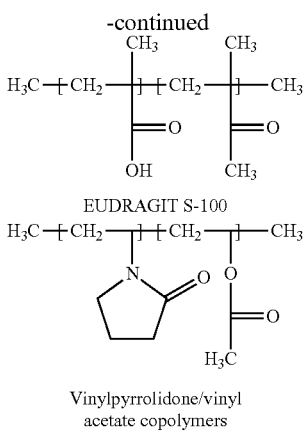

EUDRAGIT S-100

Vinylpyrrolidone/vinyl acetate copolymers

R = CH₃, C₄H₉

Desirably, for the purposes of this application, the amount of encapsulation chemistry present in the composition is between about 20 and 99.9% by weight. Alternatively, such encapsulation chemistry is present in the composition between about 40 and 90% by weight. Still in a further alternative aspect, such encapsulation chemistry is present in the composition in an amount of between about 60 and 95% by weight.

The triggerable composition can also contain other components such as solvents, plasticizers, surfactants or wettability agents, pH adjusters, and viscosity enhancers. Based on the substrate or surface on which the composition is to be deposited, or the lotion, cream, or medicament that the composition is to be used in, the composition can require addition of other ingredients to immobilize or adhere the encapsulation and trigonelline ester components more securely to the substrate, or in the formulation. The composition can also contain water-miscible or hydrophilic polymers. Furthermore, the composition can also contain other additives to adjust surface tension or other physical and chemical properties. Alternatively, the substrates can be treated with different materials to modify their surface properties before the deposition of the composition to improve the adhesion of the composition. The wettability-enhancing agent can be a single surfactant or a mixture of surfactants. The surfactants can be non-ionic, neutral surfactants, or ionic surfactants. The ionic surfactants can be either positively charged or negatively charged. Examples of non-ionic surfactants include alkyl poly(ethylene oxide) such as copolymers of poly(ethylene oxide) and poly(propylene oxide) (commercially called Poloxamers or Poloxamines), alkyl polyglucosides such as octyl glucoside and decyl maltoside, and fatty alcohols such as cetyl alcohol, oleyl alcohol, cocamide MEA and cocamide DEA. Examples of ionic surfactants include anionic (e.g., based on sulfate, sulfonate, or carboxylate anions) surfactants such as s (SDS), ammonium lauryl sulfate, and other alkyl sulfate salts, Sodium laureth sulfate, also known as sodium lauryl ether sulfate (SLES), Alkyl benzene sulfonate, soaps, and fatty acid salts; and cationic (e.g., based on quaternary ammonium cations) surfactants such as Cetyl trimethylammonium bromide (CTAB) a.k.a. hexadecyl trimethyl ammonium bromide, and other alkyltrimethylammonium salts, Cetylpyridinium chloride (CPC), Polyethoxylated tallow amine (POEA), Benzalkonium chloride (BAC), and Benzethonium chloride (BZT); or Zwitterionic (amphoteric) surfactants such as Dodecyl trigonelline, Dodecyl dimethylamine oxide, Cocamidopropyl trigonelline, and Coco ampho glycinate. Alternatively, the wettability-enhancing agents can also be hydrophilic molecules. The hydrophilic molecules can also be polymers such as polyethylene glycol and its copolymers.

The triggerable composition of the disclosure can be applied to a substrate such as an absorbent article or a layer within an absorbent article by any number of known applications or printing techniques. For example, the triggerable composition of the present disclosure can be deposited on a substrate by various surface deposition or printing methods such as brushing, flexographic printing, gravure roll printing, stamping, screen print, spraying techniques, dip and squeeze, and digital print methods. Further, the composition can be applied in a melt form and allowed to solidify on a treated substrate. As also noted, the composition can be part of a lotion, cream, or medicament as well.

Placement of the triggerable composition can be on any number of substrates. The substrate sheets can, for instance, include nonwoven or woven sheets. Such sheets can include synthetic or natural fibrous materials such as, for example, extruded spunbond, meltblown webs, bonded carded webs, airlaid materials, spun cellulosic, and wool or synthetic yarns. Such sheets can further include cellulosic-based dry or wet laid tissue or paper sheets. Additionally, such substrates can include film or foam sheets, laminates of film, foam and fibrous layers, and laminates of multiple fibrous, film, and foam layers. Such substrates/sheets can be placed as layers within medical or beauty care articles, personal care hygienic articles such as absorbent articles, or can themselves serve as the absorbent article, including as a towel, tissue, or wipe. Further, such triggerable composition can be used as components in lotions, creams, and medicaments, including tablets and suppositories.

Placement of such composition in an article or absorbent article can be across the entire article's longitudinal and transverse or lateral (width) dimensions, or on a layer of an article. Placement can be limited to certain locations within the article, or layer(s) on the article. For example, such composition can be placed at a location specifically designed to contact aqueous-based waste, such as a high-probability "soiling area" in an article's or layer's central crotch region. Such treated layers can include the topsheet layer, backsheet layer (inner surface), or absorbent core layer. Other interior-positioned layers can also be treated with the coating composition. In an alternative aspect, if a relatively hydrophobic trigonelline ester is selected for the composition (or one having relatively hydrophobic R3-R5 groups), it can be desirable to limit the placement of the coating formulation to certain locations on an absorbent article that would not directly impact the absorbency pathways of an article, such as on an inside surface of a backsheet layer (as opposed to a topsheet layer or absorbent core layer), or side areas of a topsheet layer, absorbent core layer, or other interior-positioned layer.

EXAMPLES

The following components were blended together to form coating compositions for the purpose of demonstrating the effectiveness of using a two stage triggerable composition, including an encapsulated trigonelline ester with functional active, according to the present disclosure. For some applications, those trigonelline esters need to be insulated from moisture and water before use. This issue can be solved by encapsulating the esters in a protecting matrix. The protecting matrix can either be dissolved by aqueous media or can be swollen by water to expose the esters to water for hydrolysis under various conditions. There are a number of polymers that can be used to achieve the protection while allowing water or moisture to penetrate under various conditions. For instance, dextran can be blended with the trigonelline esters to form films. Upon contact with aqueous media, the dextran is dissolved and the trigonelline esters are in contact with water for hydrolysis. For example, EUDRAGIT S-100 film can be used to provide a good matrix for trigonelline esters of vanillin to minimize the moisture sensitivity. When the trigonelline esters/EUDRAGIT S100 films are exposed to neutral water, a little vanillin was released for a long period. However, vanillin was steadily released upon exposure to an aqueous solution with a pH of 9.0.

Example 1

5 mg trigonelline ester of vanillin was added to 2 ml water and suspended by vortexing. No vanillin smell was detected. After the suspension was allowed to stay under ambient condition for 8 hours, a strong vanillin smell was detected.

Example 2

5 mg trigonelline ester of vanillin was added to 2 ml water containing 5 mg benzethenium chloride. No vanillin smell was immediately detected. The solution was allowed to stay under ambient condition for 1 hour, after which a strong vanillin smell was detected.

Example 3

3 ml PVP/VA 1-335 from ISP (100 mg/ml) in ethanol was added with 5 mg trigonelline ester of vanillin dissolved in 1 ml acetone to make a coating solution. The solution was brushed on a 24 cm×45 cm piece of polypropylene film and air-dried overnight. No vanillin smell was detected. When a piece of the coated film was exposed to water, a strong smell of vanillin was detected.

Example 4

3 ml Eudragit S-100 (100 mg/ml) in ethanol was added with 5 mg trigonelline ester of vanillin dissolved in 1 ml acetone to make a coating solution. The solution was brushed on a 24 cm×45 cm piece of polypropylene film and air-dried overnight. No vanillin smell was detected. When a piece of the coated film was exposed to water, no smell of vanillin was detected. However, a strong smell of vanillin was detected when the piece of coated film was contacted with sodium bicarbonate water solution.

As described above, in one aspect the present disclosure is directed to incorporating a two-stage triggerable composition into an absorbent article, such as a health care product including a garment or bandage, a hygiene product including a tissue or wipe, a skin-contacting beauty product including a facial wrap, or an absorbent consumer/personal care article including a feminine care pad or liner, a baby or child care diaper, or an adult incontinence garment. In particular, the composition is placed on a layer within the article and configured to release a scent, antibacterial agent, skin-repairing agent, antioxidant agent, or other functional active when exposed to a first environmental stimulus, followed by contact with an aqueous medium such as urine, menses, vaginal secretions, sweat, mucous, or a loose bowel movement. In one aspect, for instance, the composition is coated as a patch on an individual layer within a diaper, which will be exposed to an aqueous medium following contact with an initial environmental stimulus. The coated composition for example, can be coated on a portion of the topsheet layer (user facing surface or garment facing surface), the absorbent core layer (or other internal article layer), or on the inside surface of the backsheet layer. Alternatively, such coating composition can be placed on a discrete patch of separate material that functions as a carrier layer, such as, for example, a nonwoven material that includes a user-facing surface. The coating composition is released upon triggering by an environmental stimulus and contact with an aqueous medium. The two stage triggerable composition can also be made to be in particulate form and mixed with superabsorbent materials or other absorbent components as a part of an absorbent layer.

As can be seen, controlled release of chemical actives can be achieved in a two-stage process by using a stimulus-sensitive encapsulation chemistry and an aqueous medium-sensitive trigonelline ester chemistry in a single composition. Such a composition relies on two different triggering stimuli (such as pH and aqueous medium contact or enzyme and aqueous medium contact) to release an active chemistry, thereby providing stability to functional actives, and control in the graduated release of such actives to the environment or a desired location.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular aspects of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A triggerable composition for two-stage, controlled release of a functional active chemical comprising: a trigonelline ester of a functional active with at least one hydroxyl group configured to release the functional active through a hydrolysis reaction upon contact with an aqueous medium, wherein the functional active is a skin-repairing agent derived from retinol or a fragrance; and an encapsulation material for encapsulating the trigonelline ester including a functional active, the encapsulation material triggerable to release the trigonelline ester upon the occurrence of an environmental stimulus, wherein the environmental stimulus is a pH change.

2. The triggerable composition of claim 1, wherein the composition is in a form of particles, microparticles, nanoparticles, fibers, sheet, films, or a combination thereof.

3. The triggerable composition of claim 1, wherein the encapsulation material is selected from copolymers of methacrylic acid and methyl methacrylate that are sensitive to basic aqueous solutions, copolymers of dimethylaminoethyl methacrylate, butyl methacrylate, and methyl methacrylate that are sensitive to acidic aqueous solutions, and vinylpyrrolidone/vinyl acetate copolymers that are sensitive to neutral aqueous solutions.

4. The triggerable composition of claim 1, wherein the fragrance has at least one hydroxyl group selected from the group consisting of thymol, eugenol, menthol, vanillin, and combinations thereof.

5. The triggerable composition of claim 1, wherein the stimulus is a pH change from an acidic to neutral or basic environment, and wherein the encapsulation material is selected from the group consisting of copolymers of methacrylic acid and methyl methacrylate that are sensitive to basic aqueous solutions, and vinylpyrrolidone/vinyl acetate copolymers that are sensitive to neutral aqueous solutions.

6. The triggerable composition of claim 1, wherein the stimulus is a pH change from a basic to neutral or acidic environment, and wherein the encapsulation material is selected from the group consisting of copolymers of dimethylaminoethyl methacrylate, butyl methacrylate, and methyl methacrylate that are sensitive to acidic aqueous solutions, and vinylpyrrolidone/vinyl acetate copolymers that are sensitive to neutral aqueous solutions.

7. An absorbent article including at least one absorbent layer, the absorbent article including a triggerable composition for two-stage, controlled release of a functional active chemical, the triggerable composition comprising: a trigonelline ester of a functional active with at least one hydroxyl group configured to release the functional active through a hydrolysis reaction upon contact with an aqueous medium, wherein the functional active is a skin-repairing agent derived from retinol or a fragrance; and an encapsulation material for encapsulating the trigonelline ester including a functional active, the encapsulation material triggerable to release the trigonelline ester upon the occurrence of an environmental stimulus, wherein the environmental stimulus is a pH change.

8. The absorbent article of claim 7 further comprising a topsheet layer, a backsheet layer, and at least one absorbent core layer, wherein the triggerable composition is included with at least one of the topsheet layer, absorbent core layer, and the backsheet layer.

9. The absorbent article of claim 7, further comprising a carrier layer, wherein the triggerable composition is included with the carrier layer for carrying the triggerable composition within the absorbent article.

10. The absorbent article of claim 7, wherein the absorbent article is selected from the group consisting of feminine care hygiene articles, adult incontinence articles, baby and child care articles, bandages, medical garments, and skin treatment sheets.

11. The absorbent article of claim 7, wherein the fragrance has at least one hydroxyl group selected from the group consisting of thymol, eugenol, menthol, vanillin, and combinations thereof.

12. A viscous liquid comprising: a triggerable composition for two-stage, controlled release of a functional active chemical, the composition including: a trigonelline ester of a functional active with at least one hydroxyl group configured to release the functional active through a hydrolysis reaction upon contact with an aqueous medium, wherein the functional active is a skin-repairing agent derived from retinol or a fragrance, and an encapsulation material for encapsulating the trigonelline ester including a functional active, the encapsulation material triggerable to release the trigonelline ester upon the occurrence of an environmental stimulus, wherein the environmental stimulus is a pH change, wherein the viscous liquid is a lotion, cream, or medicament.

13. The viscous liquid of claim 12, wherein the fragrance has at least one hydroxyl group selected from the group consisting of thymol, eugenol, menthol, vanillin, and combinations thereof.

* * * * *